US009215969B2

(12) United States Patent
Sakai et al.

(10) Patent No.: US 9,215,969 B2
(45) Date of Patent: Dec. 22, 2015

(54) SCANNING ENDOSCOPE SYSTEM AND METHOD OF OPERATION OF SCANNING ENDOSCOPE SYSTEM

(71) Applicant: OLYMPUS MEDICAL SYSTEMS CORP., Tokyo (JP)

(72) Inventors: Yuji Sakai, Kodaira (JP); Yoshinari Okita, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 54 days.

(21) Appl. No.: 14/269,256

(22) Filed: May 5, 2014

(65) Prior Publication Data

US 2014/0303441 A1  Oct. 9, 2014

Related U.S. Application Data

(63) Continuation of application No. PCT/JP2013/076249, filed on Sep. 27, 2013.

(30) Foreign Application Priority Data

Oct. 22, 2012 (JP) ................. 2012-233022

(51) Int. Cl.
*A61B 1/07* (2006.01)
*A61B 1/00* (2006.01)
*G02B 26/10* (2006.01)

(52) U.S. Cl.
CPC ......... *A61B 1/00172* (2013.01); *A61B 1/00006* (2013.01); *A61B 1/00057* (2013.01); *A61B 1/00059* (2013.01); *A61B 1/07* (2013.01); *G02B 26/103* (2013.01)

(58) Field of Classification Search
CPC .......... A61B 1/00172; A61B 1/00006; A61B 1/00057; A61B 1/00059; A61B 1/07; A61B 5/0062; A61B 5/0064; A61B 5/0066; A61B 5/0068; G02B 26/103
USPC ........................................... 600/182
See application file for complete search history.

(56) References Cited

U.S. PATENT DOCUMENTS 6,845,190 B1 * 1/2005 Smithwick et al. ............. 385/25
7,129,472 B1 * 10/2006 Okawa et al. ................. 250/234
(Continued)

FOREIGN PATENT DOCUMENTS

JP    2011-019706 A    2/2011
JP    2011-050664 A    3/2011
(Continued)

*Primary Examiner* — John P Leubecker
(74) *Attorney, Agent, or Firm* — Scully, Scott, Murphy & Presser, PC

(57) ABSTRACT

A scanning endoscope system includes: a fiber that guides illuminating light from a light source; a first actuator provided on a side of the fiber and expands/contracts according to an applied voltage, thereby swinging the fiber; a second actuator disposed at a position facing the first actuator across the fiber and expands/contracts according to an applied voltage, thereby swinging the fiber; a drive signal output section applying a first voltage for setting a reference position of the fiber where the first actuator is in a contracted state, to the first actuator, and applying a second voltage for setting the reference position of the fiber where the second actuator is in a contracted state, to the second actuator; and a controller that in order to change the reference position of the fiber, controls the drive signal output section to change at least one of the first voltage and the second voltage.

6 Claims, 3 Drawing Sheets

(56) References Cited

U.S. PATENT DOCUMENTS

| | | | |
|---|---|---|---|
| 7,608,842 B2 * | 10/2009 | Johnston | 250/492.1 |
| 2006/0072874 A1 * | 4/2006 | Johnston | 385/25 |
| 2007/0213618 A1 * | 9/2007 | Li et al. | 600/476 |
| 2008/0165360 A1 * | 7/2008 | Johnston | 356/394 |
| 2008/0218824 A1 | 9/2008 | Johnston et al. | |
| 2009/0028407 A1 * | 1/2009 | Seibel et al. | 382/131 |
| 2011/0015528 A1 | 1/2011 | Kobayashi | |
| 2013/0155215 A1 | 6/2013 | Shimada et al. | |
| 2014/0022365 A1 * | 1/2014 | Yoshino | 348/65 |

FOREIGN PATENT DOCUMENTS

| | | |
|---|---|---|
| JP | 2011-115252 A | 6/2011 |
| JP | 2012-152244 A | 8/2012 |
| WO | WO 2012/132754 A1 | 10/2012 |

* cited by examiner

SCANNING ENDOSCOPE SYSTEM AND METHOD OF OPERATION OF SCANNING
ENDOSCOPE SYSTEM

CROSS REFERENCE TO RELATED APPLICATION

This application is a continuation application of PCT/JP2013/076249 filed on Sep. 27, 2013 and claims benefit of Japanese Application No. 2012-233022 filed in Japan on Oct. 22, 2012, the entire contents of which are incorporated herein by this reference.

BACKGROUND OF THE INVENTION

1. Field of the Invention

The present invention relates to a scanning endoscope system and a method of operation of a scanning endoscope system, and specifically relates to a scanning endoscope system and a method of operation of a scanning endoscope system for scanning an object to obtain an image.

2. Description of the Related Art

In endoscopes in a medical field, in order to reduce a burden on subjects, various techniques for thinning insertion portions to be inserted into body cavities of the subjects have been proposed. As an example of such techniques, a scanning endoscope including no solid image pickup device in a part corresponding to the aforementioned insertion portion and a system including the scanning endoscope are known.

More specifically, the system including the scanning endoscope is configured to, for example, swing a distal end portion of an illumination fiber that guides illuminating light emitted from a light source section to two-dimensionally scan an object according to a pre-set scanning pattern, receive return light from the object via light-reception fibers disposed in the periphery of the illumination fiber and generate an image of the object based on the return light received via the light-reception fibers. As an example of those having a configuration similar to such system, the scanning beam system disclosed in U.S. Patent Application Publication No. 2008/0218824 is known.

SUMMARY OF THE INVENTION

A scanning endoscope system according to an aspect of the present invention includes: a fiber that guides illuminating light emitted from a light source; a first actuator provided on a side of the fiber, the first actuator expanding/contracting according to an applied voltage, thereby swinging the fiber; a second actuator disposed at a position facing the first actuator across the fiber, the second actuator expanding/contracting according to an applied voltage, thereby swinging the fiber; a drive signal output section that applies a first voltage value for setting a reference position of the fiber where the first actuator is in a contracted state, to the first actuator, and applies a second voltage value for setting the reference position of the fiber where the second actuator is in a contracted state, to the second actuator; and a controller that in order to change the reference position of the fiber, controls the drive signal output section to change at least one of the first voltage value and the second voltage value.

A method of operation of a scanning endoscope system according to an aspect of the present invention includes the steps of: guiding illuminating light emitted from a light source, via a fiber; swinging the fiber by a first actuator provided on a side of the fiber expanding/contracting according to an applied voltage and a second actuator disposed at a position facing the first actuator across the fiber expanding/contracting according to an applied voltage; applying a first voltage value for setting a reference position of the fiber where the first actuator is in a contracted state, to the first actuator, and applying a second voltage value for setting the reference position of the fiber where the second actuator is in a contacted state, to the second actuator; and performing control to change at least one of the first voltage value and the second voltage value in order to set the reference position of the fiber.

DETAILED DESCRIPTION OF THE PREFERRED EMBODIMENT

An embodiment of the present invention will be described below with reference to the drawings.

Figure 1:
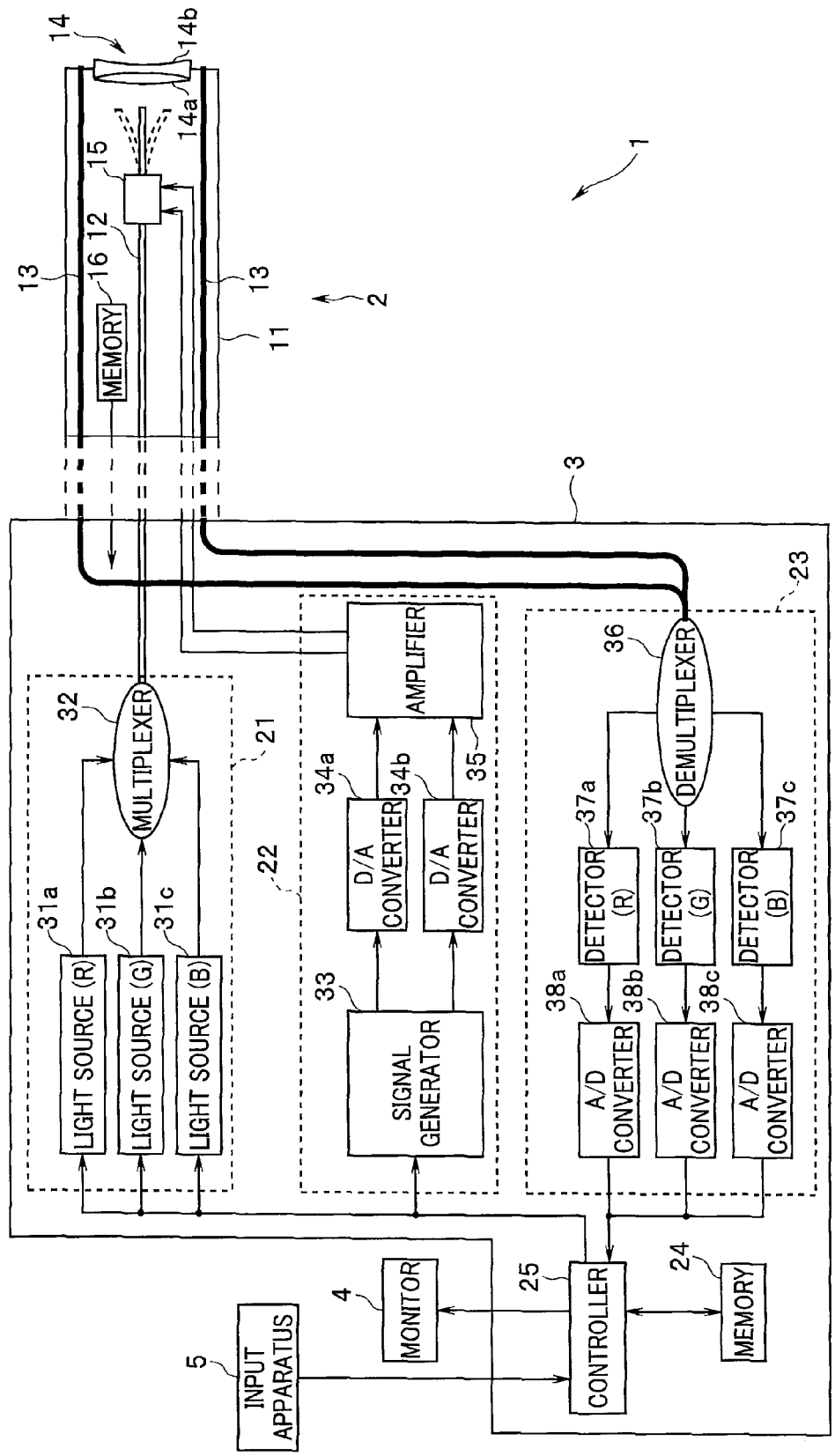
FIG. 1 is a diagram illustrating a configuration of a main part of a scanning endoscope system according to an embodiment.

FIGS. 1 to 4 relate to an embodiment of the present invention. FIG. 1 is a diagram illustrating a configuration of a main part of a scanning endoscope system according to the embodiment.

A scanning endoscope system 1 includes, for example, as illustrated in FIG. 1, a scanning endoscope 2 to be inserted into a body cavity of a subject, a body apparatus 3 to be connected to the scanning endoscope 2, a monitor 4 to be connected to the body apparatus 3 and an input apparatus 5 that enables an input of information and provision of an instruction to the body apparatus 3. Note that the input apparatus 5 is not limited to that configured as an apparatus that is separate from the body apparatus 3 such as illustrated in FIG. 1, and may be configured as, for example, an interface integrated with the body apparatus 3.

The scanning endoscope 2 includes an insertion portion 11 formed so as to have an elongated shape and flexibility that enable the insertion portion 11 to be inserted into a body cavity of a subject. Note that in a proximal end portion of the insertion portion 11, e.g., a non-illustrated connector for detachably connecting the scanning endoscope 2 to the body apparatus 3 is provided.

In a part from the proximal end portion to a distal end portion of the inside of the insertion portion 11, an illumination fiber 12 having a function as a light-guiding section that guides illuminating light supplied from a light source unit 21 of the body apparatus 3 to a light collection optical system 14, and light-reception fibers 13 that receive return light from an object and guide the return light to a detection unit 23 of the body apparatus 3 are inserted, respectively.

An end portion of the illumination fiber 12 that includes a light entrance surface is disposed in a multiplexer 32 provided inside the body apparatus 3. Also, an end portion of the illumination fiber 12 that includes a light exit surface is disposed in the vicinity of a light entrance surface of a lens 14a provided in the distal end portion of the insertion portion 11 in such a manner that the end portion is not fixed via, e.g., a fixing member.

An end portion of each light-reception fiber 13 that includes a light entrance surface is fixedly disposed in the periphery of a light exit surface of a lens 14b in a distal end face of the distal end portion of the insertion portion 11. Also, an end portion of each light-reception fiber 13 that includes a light exit surface is disposed in a demultiplexer 36 provided inside the body apparatus 3.

The light collection optical system 14 includes the lens 14a and the lens 14b, and is configured to collect illuminating light entering the lens 14a through the illumination fiber 12 and makes the collected illuminating light exit from the lens 14b to the object.

In a portion partway of the illumination fiber 12 on the distal end portion side of the insertion portion 11, an actuator section 15 that is driven based on drive signals outputted from a driver unit 22 of the body apparatus 3 is provided.

Figure 2:
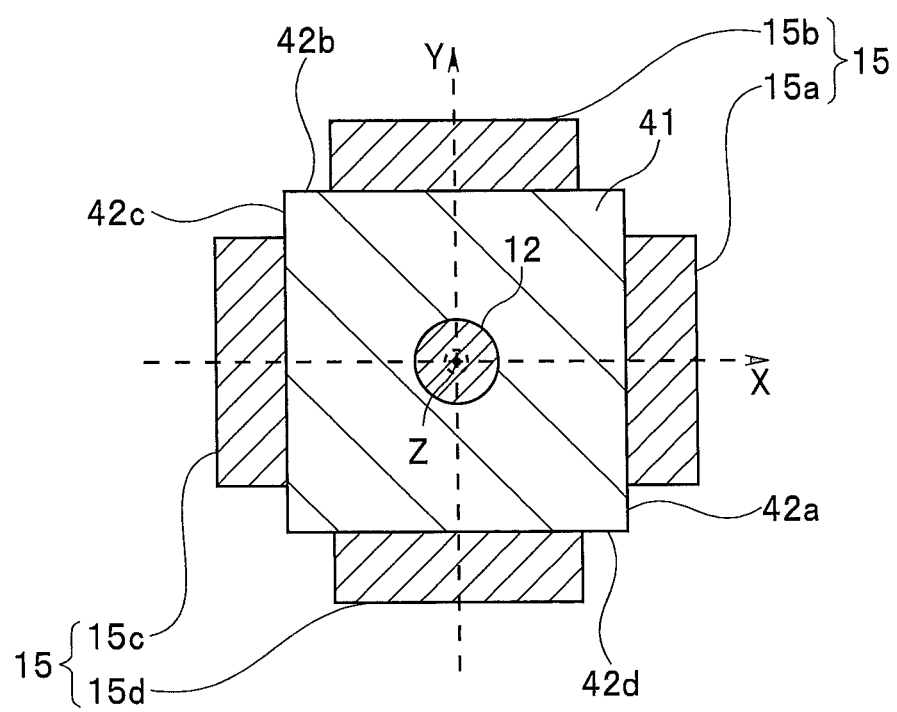
FIG. 2 is a cross-sectional diagram for describing a configuration of an actuator section provided in the scanning endoscope.

The illumination fiber 12 and the actuator section 15 are each disposed so as to have, for example, the positional relationship illustrated in FIG. 2 in a cross-section perpendicular to a longitudinal axis direction of the insertion portion 11. FIG. 2 is a cross-sectional diagram for describing a configuration of the actuator section provided in the scanning endoscope.

As illustrated in FIG. 2, a ferrule 41, which serves as a joining member, is disposed between the illumination fiber 12 and the actuator section 15. More specifically, the ferrule 41 is formed of, for example, zirconia (ceramic) or nickel.

As illustrated in FIG. 2, the ferrule 41 is formed in the shape of a quadrangular prism, and includes side faces 42a and 42c perpendicular to an X-axis direction (transverse direction in the sheet) and side faces 42b and 42d perpendicular to a Y-axis direction (vertical direction in the sheet). Also, at a center of the ferrule 41, the illumination fiber 12 is fixedly disposed. Here, the ferrule 41 may be formed in another shape other than a quadrangular prism as long as such shape is a prism.

As illustrated in FIG. 2, the actuator section 15 includes an actuator 15a disposed along the side face 42a, an actuator 15b disposed along the side face 42b, an actuator 15c disposed along the side face 42c and an actuator 15d disposed along the side face 42d.

In other words, the actuator section 15, which has a function as an optical scanning section, includes a pair of actuators 15a and 15c disposed at respective positions that face the Y-axis (or are symmetrical with respect to the Y-axis) across the illumination fiber 12, along the X-axis direction, and a pair of actuators 15b and 15d disposed at respective positions that face the X-axis (or are symmetrical with respect to the X-axis) across the illumination fiber 12, along the Y-axis direction.

Each of the actuators 15a, 15b, 15c and 15d is configured to be driven according to a drive signal outputted from the driver unit 22.

The actuator 15a includes, for example, a piezoelectric element subjected to polarization processing in advance so that a polarization direction thereof agrees with a negative direction of the X-axis (direction from the right to the left in the sheet of FIG. 2), and is configured to, upon application of a voltage of a positive value according to a drive signal outputted from the driver unit 22 (if a direction of an electric field generated as a result of supply of the drive signal is a forward direction relative to the polarization direction), contract along a Z-axis direction (normal direction in the sheet), and upon application of a voltage of a negative value according to a drive signal outputted from the driver unit 22 (if a direction of an electric field generated as a result of supply of the drive signal is a backward direction relative to the polarization direction), expand along the Z-axis direction.

The actuator 15b includes, for example, a piezoelectric element subjected to polarization processing in advance so that a polarization direction thereof agrees with a negative direction of the Y-axis (direction from the top to the bottom in the sheet of FIG. 2), and is configured to, upon application of a voltage of a positive value according to a drive signal outputted from the driver unit 22, contract along the Z-axis direction, and upon application of a voltage of a negative value according to a drive signal outputted from the driver unit 22, expand along the Z-axis direction.

The actuator 15c includes, for example, a piezoelectric element subjected to polarization processing in advance so that a polarization direction thereof agrees with the negative direction of the X-axis, and is configured to, upon application of a voltage of a negative value according to a drive signal outputted from the driver unit 22, contract along the Z-axis direction, and upon application of a voltage of a positive value according to a drive signal outputted from the driver unit 22, expand along the Z-axis direction.

The actuator 15d includes, for example, a piezoelectric element subjected to polarization processing in advance so that a polarization direction thereof agrees with the negative direction of the Y-axis, and is configured to, upon application of a voltage of a negative value according to a drive signal outputted from the driver unit 22, contract in the Z-axis direction, and upon application of a voltage of a positive value according to a drive signal outputted from the driver unit 22, expand along the Z-axis direction.

Note that according to the present embodiment, the actuator section 15 is not limited to one configured using the actuators 15a to 15d having such polarization directions and expansion/contraction directions as described above, and may be configured using actuators 15a to 15d having other polarization directions and expansion/contraction directions.

Inside the insertion portion 11, a memory 16 with endoscope information stored in advance, the endoscope information including various pieces of information such as individual identification information for the scanning endoscope 2, is provided. Upon the scanning endoscope 2 and the body apparatus 3 being connected, the endoscope information stored in the memory 16 is read from a controller 25 in the body apparatus 3.

The body apparatus 3 includes the light source unit 21, the driver unit 22, the detection unit 23, a memory 24 and the controller 25.

The light source unit 21 includes a light source 31a, a light source 31b, a light source 31c and the multiplexer 32.

The light source 31a includes, for example, a laser light source, and is configured to, when the light source 31a is controlled to be turned on by the controller 25, emit light of a red wavelength band (hereinafter also referred to as "R light") to the multiplexer 32.

The light source 31b includes, for example, a laser light source, and is configured to, when the light source 31b is controlled to be turned on by the controller 25, emit light of a green wavelength band (hereinafter also referred to as "G light") to the multiplexer 32.

The light source 31c includes, for example, a laser light source, and is configured to, when the light source 31c is controlled to be turned on by the controller 25, emit light of a blue wavelength band (hereinafter referred to as "B light") to the multiplexer 32.

The multiplexer 32 is configured to combine the R light emitted from the light source 31a, the G light emitted from the light source 31b, and the B light emitted from the light source 31c and supply the resulting light to the light entrance surface of the illumination fiber 12.

The driver unit 22 has a function as a drive signal output section, and includes a signal generator 33, D/A converters 34a and 34b and an amplifier 35.

The signal generator 33 is configured to generate respective drive signals for swinging the end portion of the illumination fiber 12 that includes the light exit surface, based on control performed by the controller 25, and output the respective drive signals to the D/A converters 34a and 34b.

The D/A converters 34a and 34b are configured to convert the respective digital drive signals outputted from the signal generator 33 into analog drive signals and output the analog drive signals to the amplifier 35.

The amplifier 35 is configured to amplify the respective drive signals outputted from the D/A converters 34a and 34b and output the resulting drive signals to the actuator section 15.

The detection unit 23 includes the demultiplexer 36, detectors 37a, 37b and 37c, and A/D converters 38a, 38b and 38c.

The demultiplexer 36 includes, e.g., a dichroic mirror, and is configured to split return light that has exited from the light exit surfaces of the light-reception fibers 13 into light of R (red) components, light of G (green) components and light of B (blue) components and make the light of R (red) components, the light of G (green) components and the light of B (blue) components exit to the respective detectors 37a, 37b and 37c.

The detector 37a is configured to detect an intensity of the R light outputted from the demultiplexer 36, generate an analog R signal according to the detected intensity of the R light and output the analog R signal to the A/D converter 38a.

The detector 37b is configured to detect an intensity of the G light outputted from the demultiplexer 36, generate an analog G signal according the detected intensity of the G light and output the analog G signal to the A/D converter 38b.

The detector 37c is configured to detect an intensity of the B light outputted from the demultiplexer 36, generate an analog B signal according to the detected intensity of the B light and output the analog B signal to the A/D converter 38c.

The A/D converter 38a is configured to convert the analog R signal outputted from the detector 37a into a digital R signal and output the digital R signal to the controller 25.

The A/D converter 38b is configured to convert the analog G signal outputted from the detector 37b into a digital G signal and output the digital G signal to the controller 25.

The A/D converter 38c is configured to convert the analog B signal outputted from the detector 37c into a digital B signal and output the digital B signal to the controller 25.

In the memory 24, e.g., a control program for performing control of the body apparatus 3 is stored in advance. Also, in the memory 24, endoscope information read by the controller 25 in the body apparatus 3 is stored.

The controller 25 includes, e.g., a CPU, and is configured to read the control program stored in the memory 24, and perform control of the light source unit 21 and the driver unit 22 based on the read control program. In other words, the actuator section 15, which has a function as an optical scanning section, can swing the illumination fiber 12 so that positions in an object illuminated by illuminating light form a trajectory according to a predetermined scanning pattern, based on drive signals outputted from the driver unit 22 according to control performed by the controller 25 such as described above.

The controller 25 operates so as to store the endoscope information outputted from the memory 16 when the insertion portion 11 is connected to the body apparatus 3, in the memory 24.

The controller 25 is configured to generate an image based on the R signal, the G signal and the B signal outputted from the detection unit 23, and display the generated image on the monitor 4.

Next, an operation, etc., of the scanning endoscope system 1 having the above described configuration will be described.

First, a user connects the scanning endoscope 2 and the monitor 4 to the body apparatus 3 and then turns on power sources of the respective components of the scanning endoscope system 1.

When power sources of the respective components of the scanning endoscope system 1 are turned on, the endoscope information stored in the memory 16 in the insertion portion 11 is read by the controller 25, and the read endoscope information is stored in the memory 24.

Next, the user disposes the scanning endoscope 2 so that a predetermined chart (not illustrated; the same applies to the below) and the distal end face of the insertion portion 11 face each other and a predetermined position in the predetermined chart and a position of an optical axis of the light collection optical system 14 (or a center of the lens 14b) are aligned with each other, and then performs an operation to turn on a predetermined switch (not illustrated; the same applies to the below) provided in the input apparatus 5 to provide an instruction to start an operation relating to adjustment of the optical axis of the scanning endoscope 2.

The controller 25 controls the light source unit 21 to switch the light sources 31a, 31b and 31c from "off" to "on", based on the instruction outputted when the predetermined switch in the input apparatus 5 is turned on, and controls the driver unit 22 to output first and second drive signals, which will be described later, from the signal generator 33.

Figure 3:
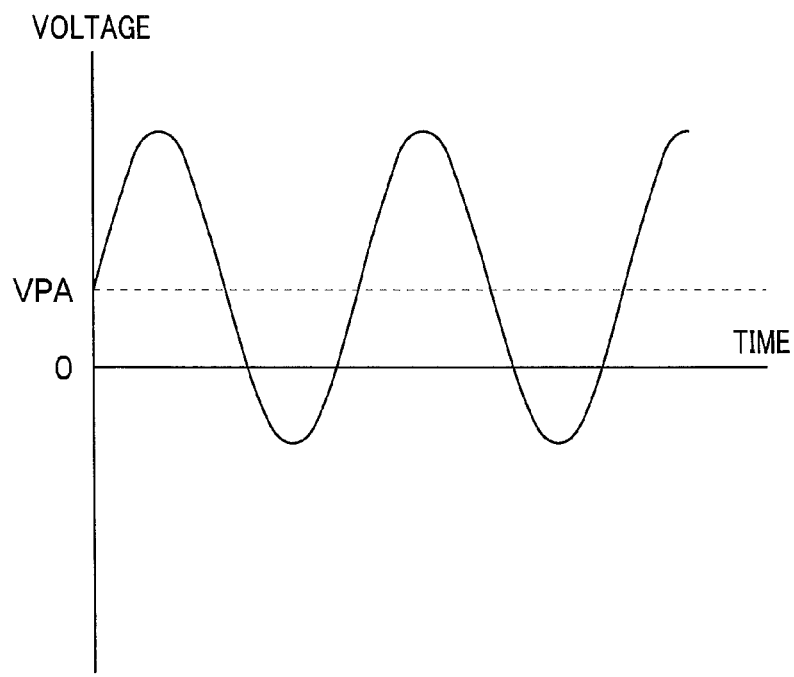
FIG. 3 is a diagram illustrating an example of a waveform of a first drive signal, which is used for driving the actuator section provided in the scanning endoscope.

Based on the control performed by the controller 25, the signal generator 33 generates a first drive signal having, for example, the waveform illustrated in FIG. 3 as a drive signal for driving the actuators 15a and 15b and outputs the first drive signal to the D/A converter 34a. FIG. 3 is a diagram illustrating an example of a waveform of the first drive signal used for driving the actuator section provided in the scanning endoscope.

More specifically, based on the control performed by the controller 25, the signal generator 33 generates a sine wave whose voltage value periodically varies with, for example, a positive voltage value VPA that is larger than zero as a center, as a first drive signal (see FIG. 3).

Figure 4:
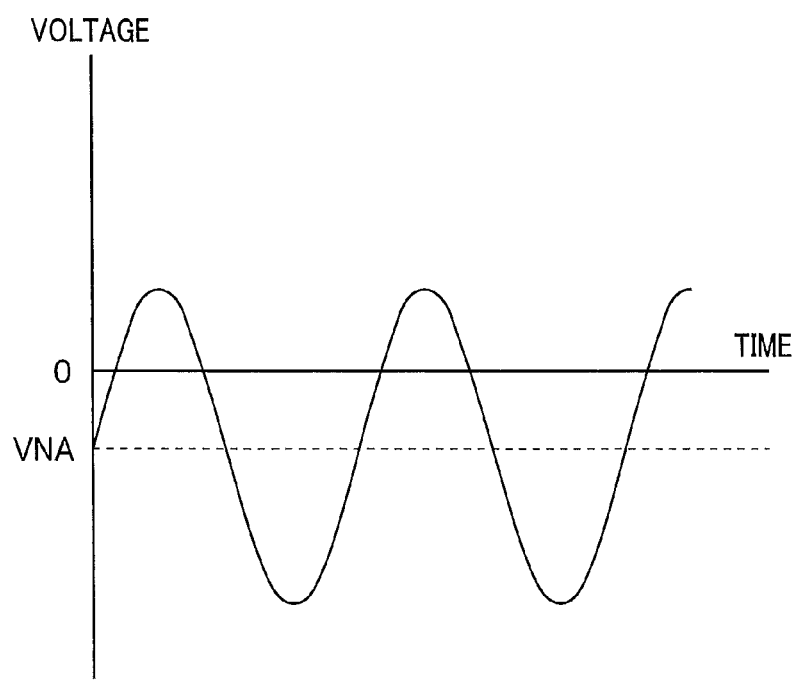
FIG. 4 is a diagram illustrating an example of a waveform of a second drive signal, which is used for driving the actuator section provided in the scanning endoscope.

Also, based on the control performed by the controller 25, the signal generator 33 generates a second drive signal having, for example, the waveform illustrated in FIG. 4 as a drive signal for driving the actuators 15c and 15d and outputs the second drive signal to the D/A converter 34b. FIG. 4 is a diagram illustrating an example of a waveform of the second drive signal used for driving the actuator section provided in the scanning endoscope.

More specifically, based on the control performed by the controller 25, the signal generator 33 generates a sine wave whose voltage value periodically varies with, for example, a negative voltage value VNA that is smaller than zero as a center, as a second drive signal (see FIG. 4).

Note that in the present embodiment, the above-described first and second drive signals are generated as signals having a same phase.

The first drive signal generated by the signal generator 33 is outputted to the actuators 15a and 15b through the D/A converter 34a and the amplifier 35. Also, the second drive signal generated by the signal generator 33 is outputted to the actuators 15c and 15d through the D/A converter 34b and the amplifier 35. Then, as a result of the actuator section 15 being driven by the first and second drive signals such as illustrated in FIGS. 3 and 4, the illumination fiber 12 is swung in a circular or elliptical scanning pattern.

The user makes a visual observation of the positions in the predetermined chart sequentially illuminated by the illuminating light from the scanning endoscope 2 to check whether or not the predetermined position in the predetermined chart and a center position of a circular or elliptical trajectory formed by the positions illuminated by the illuminating light are aligned with each other.

Subsequently, if a user confirms that the predetermined position in the predetermined chart and the center position of the circular or elliptical trajectory formed by the positions in the predetermined chart illuminated by the illuminating light are not aligned with each other, the user operates a predetermined input interface (not illustrated; the same applies to the below) provided in the input apparatus 5 (while remaining the disposition of the scanning endoscope 2 unchanged) to provide an instruction to change at least one of the positive voltage value VPA and the negative voltage value VNA.

Based on the instruction from the predetermined input interface of the input apparatus 5, the controller 25 controls the driver unit 22 to individually increase or decrease the positive voltage value VPA for the first drive signal and the negative voltage value VNA for the second drive signal.

Then, if the user confirms that the predetermined position in the predetermined chart and the center position of the circular or elliptical trajectory formed by the positions illuminated by the illuminating light are aligned with each other as a result of operating the predetermined input interface in the input apparatus 5 while making a visual observation of the positions in the predetermined chart sequentially illuminated by illuminating light from the scanning endoscope 2, the user performs an operation to turn off the predetermined switch in the input apparatus 5 to provide an instruction to terminate the operation relating to the adjustment of the optical axis of the scanning endoscope 2.

Based on the instruction outputted when the predetermined switch in the input apparatus 5 is turned off, the controller 25 controls the light source unit 21 to switch the light sources 31a, 31b and 31c from "on" to "off", and controls the driver unit 22 to stop the outputs of the first and second drive signals from the signal generator 33.

Also, the controller 25 stores respective set values for the positive voltage value VPA and the negative voltage value VNA at the timing of the turn-off of the predetermined switch in the input apparatus 5, in the memory 24 in association with the endoscope information read from the memory 16.

In other words, according to the present embodiment, for example, if endoscope information that is the same as that read from the memory 16 when the scanning endoscope 2 is connected to the body apparatus 3 is already stored in the memory 24, the driver unit 22 can be controlled to output a first drive signal having the set value for the positive voltage value VPA associated with the endoscope information and also output a second drive signal having the set value for the negative voltage value VNA associated with the endoscope information.

Also, the present embodiment is not limited to one configured so that set values for a positive voltage value VPA and a negative voltage value VNA at the timing of turn-off of the first switch are stored in the memory 24, and may be, for example, one configured to store the set values in the memory 16. Such configuration enables control of (enables the controller 25 to control) the driver unit 22 to, for example, as a result of the endoscope information and the set values for the positive voltage value VPA and the negative voltage value VNA being read from the memory 16 when the scanning endoscope 2 is connected to the body apparatus 3, output a first drive signal having the read set value for the positive voltage value VPA and a second drive signal having the read set value for the negative voltage value VNA.

In other words, in the memory 16 and (or) the memory 24, the respective set values for the positive voltage value VPA and the negative voltage value VNA that enable correction of a misalignment between the optical axis of the light collection optical system 14 and the center position of the trajectory of positions illuminated by illuminating light, the trajectory being formed according to the predetermined scanning pattern, and the endoscope information including various pieces of information such as individual identification information for the scanning endoscope 2 are stored.

As described above, the present embodiment enables correction of a misalignment between a center position when an object is scanned in a predetermined scanning pattern (center position of a trajectory of positions illuminated by illuminating light, the trajectory being formed according to a predetermined scanning pattern) and the optical axis of the light collection optical system 14 by adjusting a positive voltage value VPA and a negative voltage value VNA. As a result, the present embodiment enables easy adjustment of an optical axis of a scanning endoscope.

It should be understood that: the present invention is not limited to the above-described embodiment; and various modifications and applications are possible without departing from the spirit of the invention.

What is claimed is:

1. A scanning endoscope system comprising:
a fiber that guides illuminating light emitted from a light source;
a first actuator provided on a side of the fiber, the first actuator contracting according to a value of an applied positive voltage, thereby swinging the fiber;
a second actuator disposed at a position facing the first actuator across the fiber, the second actuator contracting according to a value of an applied negative voltage, thereby swinging the fiber;
a drive signal output section that applies, to the first actuator, a drive signal for driving the first actuator, the drive signal having a waveform with a positive voltage at the center, and applies, to the second actuator, a drive signal for driving the second actuator, the drive signal having a waveform with a same phase as a phase of the drive signal for driving the first actuator, the waveform having a negative voltage at the center; and
a controller that controls to change at least one of the positive voltage which is at the center of the waveform of the drive signal for driving the first actuator applied by the drive signal output section, and the negative voltage at the center of the waveform of the drive signal for driving the second actuator.

2. The scanning endoscope system according to claim 1 further comprising:
a light collection optical system that collects the illuminating light entered through the fiber to make the illuminating light exit toward an object; and
a memory that stores respective set values for the value of the positive voltage and the value of the negative voltage for correcting a misalignment between an optical axis of the light collection optical system and the reference position of the fiber.

3. The scanning endoscope system according to claim 2 further comprising:

a light-receiving section that receives return light of the illuminating light applied to the object;

a light-detecting section configured to generate a signal according to an intensity of the return light received by the light-receiving section and output the signal; and an image-generating section configured to generate an image of the object based on the signal outputted from the light-detecting section.

4. The scanning endoscope system according to claim 1 further comprising:

an input section that allows provision of an instruction to individually change the set values for the value of the positive voltage and the value of the negative voltage; and a memory that stores the set values for the value of the positive voltage and the value of the negative voltage changed according to the instruction provided via the input section.

5. The scanning endoscope system according to claim 1, wherein each of the first actuator and the second actuator includes a piezoelectric element subjected to polarization processing in advance so that the first actuator and the second actuator have a same polarization direction along a predetermined axis direction.

6. A method of operation of a scanning endoscope system, the method comprising the steps of:

guiding illuminating light emitted from a light source, via a fiber;

swinging the fiber through contraction of a first actuator provided on a side of the fiber according to a value of an applied positive voltage;

swinging the fiber through contraction of a second actuator disposed at a position facing the first actuator across the fiber according to a value of an applied negative voltage;

a drive signal output section applying, to the first actuator, a drive signal for driving the first actuator, the drive signal having a waveform with a positive voltage at the center, and applying, to the second actuator, a drive signal for driving the second actuator, the drive signal having a waveform with a same phase as a phase of the drive signal for driving the first actuator, the waveform having a negative voltage at the center; and a controller performing control to change at least one of the positive voltage which is at the center of the waveform of the drive signal for driving the first actuator applied by the drive signal output section, and the negative voltage at the center of the waveform of the drive signal for driving the second actuator.

* * * * *